(12) United States Patent
Li et al.

(10) Patent No.: US 11,679,097 B2
(45) Date of Patent: Jun. 20, 2023

(54) COMBINATION PRODUCT CONTAINING LIMONOID COMPOUND AND BIGUANIDE COMPOUND

(71) Applicant: ZHEJIANG YANGSHENGTANG INSTITUTE OF NATURAL MEDICATION CO., LTD., Hangzhou (CN)

(72) Inventors: Dong Li, Hangzhou (CN); Quan Han, Hangzhou (CN); Liu Hu, Hangzhou (CN); Lian Xue, Hangzhou (CN)

(73) Assignee: ZHEJIANG YANGSHENGTANG INSTITUTE OF NATURAL MEDICATION CO., LTD., Hangzhou (CN)

(*) Notice: Subject to any disclaimer, the term of this patent is extended or adjusted under 35 U.S.C. 154(b) by 458 days.

(21) Appl. No.: 16/637,018

(22) PCT Filed: Jul. 13, 2018

(86) PCT No.: PCT/CN2018/095615
§ 371 (c)(1),
(2) Date: Feb. 6, 2020

(87) PCT Pub. No.: WO2019/029319
PCT Pub. Date: Feb. 14, 2019

(65) Prior Publication Data
US 2022/0125757 A1 Apr. 28, 2022

(30) Foreign Application Priority Data
Aug. 8, 2017 (CN) .......................... 201710670354.0

(51) Int. Cl.
| | | |
|---|---|---|
| *A61K 31/366* | (2006.01) | |
| *A61K 31/155* | (2006.01) | |
| *A61K 31/585* | (2006.01) | |
| *A61K 31/7048* | (2006.01) | |
| *C07J 73/00* | (2006.01) | |
| *A61P 3/04* | (2006.01) | |
| *A61P 3/10* | (2006.01) | |
| *A61P 3/00* | (2006.01) | |

(52) U.S. Cl.
CPC .......... *A61K 31/366* (2013.01); *A61K 31/155* (2013.01); *A61K 31/585* (2013.01); *A61K 31/7048* (2013.01); *A61P 3/04* (2018.01); *A61P 3/10* (2018.01)

(58) Field of Classification Search
CPC .. A61K 31/366; A61K 31/155; A61K 31/585; A61K 31/7048; A61K 2300/00; A61P 3/04; A61P 3/10; A61P 3/00; C07J 73/00
See application file for complete search history.

(56) References Cited

U.S. PATENT DOCUMENTS

| | | |
|---|---|---|
| 2012/0177730 A1 | 7/2012 | Baron et al. |
| 2014/0371303 A1 | 12/2014 | Guthrie |
| 2017/0165310 A1 | 6/2017 | Horiba |

FOREIGN PATENT DOCUMENTS

| | | | |
|---|---|---|---|
| CN | 101330921 | A | 12/2008 |
| CN | 102481276 | * | 5/2012 |
| CN | 102481276 | A | 5/2012 |
| CN | 103402358 | A | 11/2013 |
| CN | 103597071 | A | 2/2014 |
| CN | 106132425 | A | 11/2016 |
| WO | WO-2007/031830 | A2 | 3/2007 |
| WO | WO-2007/031830 | A3 | 3/2007 |
| WO | WO-2010/123930 | A2 | 10/2010 |
| WO | WO-2010/123930 | A3 | 10/2010 |
| WO | WO-2012/054526 | A2 | 4/2012 |
| WO | WO-2012/054526 | A3 | 4/2012 |
| WO | WO-2012/094636 | A2 | 7/2012 |
| WO | WO-2012/094636 | A3 | 7/2012 |
| WO | WO-2014/049366 | A1 | 4/2014 |
| WO | WO-2014/203059 | A1 | 12/2014 |

OTHER PUBLICATIONS

CN102481276—machine-translation, 2022, machine translation of CN102481276.*
Obacunone, 2022, pubchem compound.*
Sessions et al., Organic Letters, 2007, 9(17), 3221-3224.*
International Search Report and Written Opinion of the International Searching Authority dated Sep. 30, 2018, for PCT Application No. PCT/CN2018/095615, filed on Jul. 13, 2018, 10 pages (with English translation).
Sun Chongde et al. (2004). "Extraction, identification and determination of natural limonin and nomolin from citrus fruits," Journal of Chinese Institute of Food Service and Technology 4:6-11 (with English translation).
Shin Hasegawa, et al. (1994). "Biochemistry of Citrus Limonoids—Metabolism and Biological Functions," Journal of the Japanese Society of Food Science and Technology, vol. 41, No. 5, pp. 372-380 (Partial English Translation Provided).
Database WPI Week Aug. 2017, Thomson Scientific, London, GB; AN 2016-676777 and CN 105 950 184, 2017, 2 total pages.
Extended European Search Report dated Apr. 19, 2021, for EP Application No. 18 842 956.7, filed on Jul. 13, 2018, 9 pages.

* cited by examiner

*Primary Examiner* — Sun Jae Yoo
(74) *Attorney, Agent, or Firm* — Cooley LLP

(57) ABSTRACT

The present invention relates to a combination product comprising a limonoid compound (or a pharmaceutically acceptable derivative, ester, stereoisomer, salt or prodrug thereof), and a biguanide compound (e.g., metformin, metformin hydrochloride, buformin, and phenformin). The present invention further relates to a use of the combination product for prevention and/or treatment of a disease associated with diabetes, for lipid-lowering and weight-loss, and the like.

8 Claims, No Drawings

COMBINATION PRODUCT CONTAINING LIMONOID COMPOUND AND BIGUANIDE COMPOUND

RELATED APPLICATIONS

This application is a U.S. National Phase application, filed under 35 U.S.C. § 371(c), of International Application No. PCT/CN2018/095615, filed Jul. 13, 2018, which claims priority to, and the benefit of, Chinese Patent Application No. 201710670354.0, filed Aug. 8, 2017, and the entire contents of both of which are herein incorporated by reference.

TECHNICAL FIELD

The present invention belongs to the technical field of medicine, and particularly relates to a combination product comprising a limonoid compound (and a pharmaceutically acceptable derivative, ester, stereoisomer, salt or prodrug thereof) and a biguanide compound (or a pharmaceutically acceptable salt thereof). The present invention also relates to the use of the combination product in the treatment and/or prevention of a disease associated with diabetes, obesity and metabolic syndrome.

BACKGROUND ART

According to IDF statistics, there were about 415 million people with diabetes worldwide in 2015, i.e., 1 out of every 11 people has diabetes. The number of diabetic patients in China is about 110 million, ranking first in the world. It is predicted that by 2040, 642 million people worldwide will have diabetes, and the diabetic patients in China will reach 151 million. Diabetes requires life-long monitoring and treatment, and if not being well controlled, it will lead to secondary cardiovascular diseases, blindness, stroke, diabetic nephropathy, diabetic gangrene and other complications in patients, which will seriously endanger human health and life.

More than 90% of diabetes is type II diabetes, and oral hypoglycemic agents are the main treatment method. At present, the main oral drugs include: sulfonylureas, biguanides, α-glucosidase inhibitors, thiazolidinediones, DPP-4 inhibitors, etc., but the oral hypoglycemic drugs are prone to severe side effects such as drug resistance, low blood sugar, and toxicity to liver and kidney. For example, biguanide compounds have a hypoglycemic effect, but it is known at the same time according to the existing clinical data that the administration thereof may lead to lactic acid accumulation in patients with renal impairment or defect, which cause lactic acidosis, so that there is a certain risk of toxic side effects. Biguanide compounds, such as metformin, are commonly used in their hydrochloride salts, which are white crystals or crystalline powder, odorless, soluble in water, soluble in methanol, slightly soluble in ethanol, insoluble in chloroform or ether. Their side effects are mainly (1) nausea, vomiting, diarrhea, abdominal pain, abdominal distension, indigestion, fatigue, etc.; (2) tiredness, weight loss, headache, dizziness, abnormal taste, rash, chills, flu-like symptoms, palpitations, flushing, etc.; (3) lactic acidosis, manifested as vomiting, abdominal pain, excessive ventilation, and disturbance of consciousness.

The limonoid compounds are mainly present in fruits of rutaceous plants, such as immature bitter orange, navel orange, citrus, orange, pomelo and the like. Their contents are higher in the cores (seeds), and lower in the peel (about 1/10,000 to 5/100,000). About 50 kinds of limonoid compounds have been isolated and identified from citrus plants. The limonoid compounds have various biological activities such as antitumor, insect antifeedant, antiviral, analgesic, anti-inflammatory and hypnotic, and can be used in functional food additives, anti-cancer foods, pesticides, feed additives, etc.

Considering the hypoglycemic effect and side effects of biguanide compounds, there is an unmet need for a pharmaceutical combination product that is simple to take, good in effect, and low in side effects.

CONTENTS OF THE INVENTION

The present invention provides a combination product comprising a limonoid compound and a biguanide compound, and a use of this combination product for prevention and/or treatment of a disease associated with diabetes, obesity and metabolic syndrome. Compared with biguanide compounds or limonoid compounds as monotherapy at the same dose, the combination product containing a limonoid compound and a biguanide compound as mentioned in the present invention can significantly enhance therapeutic effects such as hypoglycemic, hypolipidemic and weight-losing effects, and show synergistic effect. At the same time, the amount of biguanide compounds is reduced, thereby reducing its side effects.

In a first aspect of the present invention, there is provided a combination product comprising a limonoid compound (or a pharmaceutically acceptable derivative, ester, stereoisomer, salt or prodrug thereof), and a biguanide compound (or a pharmaceutically acceptable salt thereof), or a combination product comprising only a limonoid (or a pharmaceutically acceptable derivative, ester, stereoisomer, salt or prodrug thereof), and a biguanide compound (or a pharmaceutically acceptable salt thereof) as active ingredients.

The limonoid compounds as mentioned in the present invention are a general term for a class of highly oxidized compounds or derivatives thereof with a 4,4,8-trimethyl-17-furanosteroid skeleton (or can be expressed as compounds consisting of variants of furanolactone polycyclic core structure, and having four fused 6-membered rings and one furan ring). Specifically, the examples of the limonoid compounds include, but are not limited to: limonin, isolimonic acid, 7α-limonol, obacunone, ichangin, ichangensin, nomilin, deacetylnomilin, nomilin acid, deacetylnomilin acid, citrusin, isoobacunoic acid, etc., and any glycoside derivatives thereof. The structural formula of an exemplary limonoid compound, i.e., limonin, is shown below.

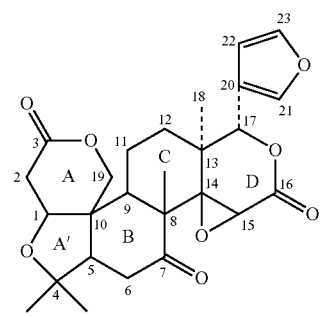

Structural formula of limonin

Further, the glucoside derivatives of the limonoid compounds as mentioned in the present invention include, but are not limited to: limonin 17-β-D-glucopyranoside, ichangin 17-β-D-glucopyranoside, isolimonic acid 17-β-D-glucopyranoside, deactylnomilin 17-β-D-glucopyranoside, nomilin 17-β-D-glucopyranoside, obacunone 17-β-D-glucopynoside, nomilinic acid 17-β-D-glucopyranoside, deacetylnomilinic acid 17-β-D-glucopyranoside, etc.

In some embodiments, the limonoid compounds as mentioned in the present invention are in the form of a monomer or an extract. The monomer is extracted or artificially synthesized, and its sources may be commercially available, or they can be easily prepared and obtained by the prior art in the art.

The biguanide compounds as mentioned in the present invention include, but are not limited to, metformin, buformin, phenformin, and the like. N,N-dimethylimidodicarbonimidic diamide is often referred to as metformin or 1,1-metformin. Metformin may exist in the form of a free base, or it may form a salt, including its pharmaceutically acceptable salt, such as a hydrochloride salt (e.g., a monohydrochloride salt). The term "metformin" as used herein is not limited to its free base, but also includes metformin salts, such as the pharmaceutically acceptable salts of metformin, the hydrochloride and monohydrochloride of metformin.

In some embodiments, the combination product is in the form of a pharmaceutical composition, and the pharmaceutical composition is in a unit dosage form.

In some embodiments, the limonoid compound (or a pharmaceutically acceptable derivative, ester, stereoisomer, salt, or prodrug thereof) and the biguanide compound (or a pharmaceutically acceptable compound thereof) are each in the form of a separate preparation. Further, the limonoid compound (or a pharmaceutically acceptable derivative, ester, stereoisomer, salt or prodrug thereof) and the biguanide compound (or a pharmaceutically acceptable salt thereof) are each in the form of a separate unit dosage form. Further, the limonoid compound (or a pharmaceutically acceptable derivative, ester, stereoisomer, salt or prodrug thereof) and the biguanide compound (or a pharmaceutically acceptable salt thereof) can be administered simultaneously or sequentially.

In some embodiments, the biguanide has an amount of 10 mg, 20 mg, 40 mg, 50 mg, 75 mg, 100 mg, 150 mg, 200 mg, 250 mg, 300 mg, 375 mg, 500 mg, 750 mg, 1500 mg, 1875 mg, or 2000 mg, and the ranges between these amounts, wherein the ranges include but are not limited to: 10 mg to 20 mg, 10 mg to 40 mg, 10 mg to 50 mg, 10 mg to 75 mg, 10 mg to 100 mg, 10 mg to 150 mg, 10 mg to 200 mg, 10 mg to 250 mg, 10 mg to 300 mg, 10 mg to 375 mg, 10 mg to 500 mg, 10 mg to 750 mg, 10 mg to 1500 mg, 10 mg to 1875 mg, 10 mg to 2000 mg, 20 mg to 40 mg, 20 mg to 50 mg, 20 mg to 75 mg, 20 mg to 100 mg, 20 mg to 150 mg, 20 mg to 200 mg, 20 mg to 250 mg, 20 mg to 300 mg, 20 mg to 375 mg, 20 mg to 500 mg, 20 mg to 750 mg, 20 mg to 1500 mg, 20 mg to 1875 mg, 20 mg to 2000 mg, 40 mg to 50 mg, 40 mg to 75 mg, 40 mg to 100 mg, 40 mg to 150 mg, 40 mg to 200 mg, 40 mg to 250 mg, 40 mg to 300 mg, 40 mg to 375 mg, 40 mg to 500 mg, 40 mg to 750 mg, 40 mg to 1500 mg, 40 mg to 1875 mg, 40 mg to 2000 mg, 50 mg to 75 mg, 50 mg to 100 mg, 50 mg to 150 mg, 50 mg to 200 mg, 50 mg to 250 mg, 50 mg to 300 mg, 50 mg to 375 mg, 50 mg to 500 mg, 50 mg to 750 mg, 50 mg to 1500 mg, 50 mg to 1875 mg, 50 mg to 2000 mg, 75 mg to 100 mg, 75 mg to 150 mg, 75 mg to 200 mg, 75 mg to 250 mg, 75 mg to 300 mg, 75 mg to 375 mg, 75 mg to 500 mg, 75 mg to 750 mg, 75 mg to 1500 mg, 75 mg to 1875 mg, 75 mg to 2000 mg, 100 mg to 150 mg, 100 mg to 200 mg, 100 mg to 250 mg, 100 mg to 300 mg, 100 mg to 375 mg, 100 mg to 500 mg, 100 mg to 750 mg, 100 mg to 1500 mg, 100 mg to 1875 mg, 100 mg to 2000 mg, 150 mg to 200 mg, 150 mg to 250 mg, 150 mg to 300 mg, 150 mg to 375 mg, 150 mg to 500 mg, 150 mg to 750 mg, 150 mg to 1500 mg, 150 mg to 1875 mg, 150 mg to 2000 mg, 200 mg to 250 mg, 200 mg to 300 mg, 200 mg to 375 mg, 200 mg to 500 mg, 200 mg to 750 mg, 200 mg to 1500 mg, 200 mg to 1875 mg, 200 mg to 2000 mg, 250 mg to 300 mg, 250 mg to 375 mg, 250 mg to 500 mg, 250 mg to 750 mg, 250 mg to 1500 mg, 250 mg to 1875 mg, 250 mg to 2000 mg, 300 mg to 375 mg, 300 mg to 500 mg, 300 mg to 750 mg, 300 mg to 1500 mg, 300 mg to 1875 mg, 300 mg to 2000 mg, 375 mg to 500 mg, 375 mg to 750 mg, 375 mg to 1500 mg, 375 mg to 1875 mg, 375 mg to 2000 mg, 500 mg to 750 mg, 500 mg to 1500 mg, 500 mg to 1875 mg, 500 mg to 2000 mg, 750 mg to 1500 mg, 750 mg to 1875 mg, 750 mg to 2000 mg, and 1875 mg to 2000 mg.

In some embodiments, the limonoid compound has an amount of 10 mg, 20 mg, 40 mg, 50 mg, 75 mg, 100 mg, 150 mg, 200 mg, 250 mg, 300 mg, 375 mg, 500 mg, 750 mg, 1500 mg, 1875 mg, or 2000 mg, and the ranges between these amounts, wherein the ranges include but are not limited to: 10 mg to 20 mg, 10 mg to 40 mg, 10 mg to 50 mg, 10 mg to 75 mg, 10 mg to 100 mg, 10 mg to 150 mg, 10 mg to 200 mg, 10 mg to 250 mg, 10 mg to 300 mg, 10 mg to 375 mg, 10 mg to 500 mg, 10 mg to 750 mg, 10 mg to 1500 mg, 10 mg to 1875 mg, 10 mg to 2000 mg, 20 mg to 40 mg, 20 mg to 50 mg, 20 mg to 75 mg, 20 mg to 100 mg, 20 mg to 150 mg, 20 mg to 200 mg, 20 mg to 250 mg, 20 mg to 300 mg, 20 mg to 375 mg, 20 mg to 500 mg, 20 mg to 750 mg, 20 mg to 1500 mg, 20 mg to 1875 mg, 20 mg to 2000 mg, 40 mg to 50 mg, 40 mg to 75 mg, 40 mg to 100 mg, 40 mg to 150 mg, 40 mg to 200 mg, 40 mg to 250 mg, 40 mg to 300 mg, 40 mg to 375 mg, 40 mg to 500 mg, 40 mg to 750 mg, 40 mg to 1500 mg, 40 mg to 1875 mg, 40 mg to 2000 mg, 50 mg to 75 mg, 50 mg to 100 mg, 50 mg to 150 mg, 50 mg to 200 mg, 50 mg to 250 mg, 50 mg to 300 mg, 50 mg to 375 mg, 50 mg to 500 mg, 50 mg to 750 mg, 50 mg to 1500 mg, 50 mg to 1875 mg, 50 mg to 2000 mg, 75 mg to 100 mg, 75 mg to 150 mg, 75 mg to 200 mg, 75 mg to 250 mg, 75 mg to 300 mg, 75 mg to 375 mg, 75 mg to 500 mg, 75 mg to 750 mg, 75 mg to 1500 mg, 75 mg to 1875 mg, 75 mg to 2000 mg, 100 mg to 150 mg, 100 mg to 200 mg, 100 mg to 250 mg, 100 mg to 300 mg, 100 mg to 375 mg, 100 mg to 500 mg, 100 mg to 750 mg, 100 mg to 1500 mg, 100 mg to 1875 mg, 100 mg to 2000 mg, 150 mg to 200 mg, 150 mg to 250 mg, 150 mg to 300 mg, 150 mg to 375 mg, 150 mg to 500 mg, 150 mg to 750 mg, 150 mg to 1500 mg, 150 mg to 1875 mg, 150 mg to 2000 mg, 200 mg to 250 mg, 200 mg to 300 mg, 200 mg to 375 mg, 200 mg to 500 mg, 200 mg to 750 mg, 200 mg to 1500 mg, 200 mg to 1875 mg, 200 mg to 2000 mg, 250 mg to 300 mg, 250 mg to 375 mg, 250 mg to 500 mg, 250 mg to 750 mg, 250 mg to 1500 mg, 250 mg to 1875 mg, 250 mg to 2000 mg, 300 mg to 375 mg, 300 mg to 500 mg, 300 mg to 750 mg, 300 mg to 1500 mg, 300 mg to 1875 mg, 300 mg to 2000 mg, 375 mg to 500 mg, 375 mg to 750 mg, 375 mg to 1500 mg, 375 mg to 1875 mg, 375 mg to 2000 mg, 500 mg to 750 mg, 500 mg to 1500 mg, 500 mg to 1875 mg, 500 mg to 2000 mg, 750 mg to 1500 mg, 750 mg to 1875 mg, 750 mg to 2000 mg, and 1875 mg to 2000 mg.

In some embodiments, the biguanide compound is selected from metformin, metformin hydrochloride, buformin, and phenformin, and the limonoid compound is selected from one or more of: limonin, isolimonic acid, 7α-limonol, obacunone, ichangin, ichangensin, nomilin, deacetylnomilin, nomilin acid, deacetylnomilin acid, citrusin, isoobacunoic acid, etc., and any glycoside derivatives thereof.

In some embodiments, the combination product further comprises a pharmaceutically acceptable carrier, diluent, or excipient.

In some embodiments, the combination product is in the form of tablet, capsule, granule, syrup, powder, lozenge, sachet, cachet, elixir, suspension, emulsion, solution, syrup, aerosol, ointment, cream and injection.

In a second aspect of the present invention, there is provided a use of the combination product in manufacture of a medicament for the prevention and/or treatment of a disease associated with diabetes, obesity, and metabolic syndrome. In some embodiments, the diabetes is type I diabetes. In some embodiments, the diabetes is type II diabetes.

In a third aspect of the present invention, there is provided a method of administering the limonoid compound (or a pharmaceutically acceptable derivative, ester, stereoisomer, salt or prodrug thereof) and the biguanide compound (or a pharmaceutically acceptable salt thereof) in combination to prevent and/or treat a disease. In some embodiments, there is provided a method of administering the limonoid compound (or a pharmaceutically acceptable derivative, ester, stereoisomer, salt or prodrug thereof) and the biguanide compound (or a pharmaceutically acceptable salt thereof) in combination to prevent and/or treat a disease associated with diabetes, obesity, and metabolic syndrome. In some embodiments, there is provided a method of administering the limonoid compound (or a pharmaceutically acceptable derivative, ester, stereoisomer, salt or prodrug thereof) and the biguanide compound (or a pharmaceutically acceptable salt thereof) in combination to lower a blood glucose. In some embodiments, there is provided a method of administering the limonoid compound (or a pharmaceutically acceptable derivative, ester, stereoisomer, salt or prodrug thereof) and the biguanide compound (or a pharmaceutically acceptable salt thereof) in combination to improve an insulin sensitivity. In some embodiments, there is provided a method of administering the limonoid compound (or a pharmaceutically acceptable derivative, ester, stereoisomer, salt or prodrug thereof) and the biguanide compound (or a pharmaceutically acceptable salt thereof) in combination to improve a leptin sensitivity. In some embodiments, there is provided a method of administering the limonoid compound (or a pharmaceutically acceptable derivative, ester, stereoisomer, salt or prodrug thereof) and the biguanide compound (or a pharmaceutically acceptable salt thereof) in combination to reduce a content of serum cholesterol and serum triglyceride. In some embodiments, there is provided a method of administering the limonoid compound (or a pharmaceutically acceptable derivative, ester, stereoisomer, salt or prodrug thereof) and the biguanide compound (or a pharmaceutically acceptable salt thereof) in combination to reduce a body weight.

In some embodiments, the limonoid compound (or a pharmaceutically acceptable derivative, ester, stereoisomer, salt or prodrug thereof) and the biguanide compound (or a pharmaceutically acceptable salt thereof) can be mixed into a preparation form and administered in the form of a pharmaceutical composition (preferably, a dosage unit form); in some embodiments, the limonoid compound (or a pharmaceutically acceptable derivative, ester, stereoisomer, salt or prodrug thereof) and the biguanide compound (or a pharmaceutically acceptable salt thereof) are each in separate preparation form (preferably, each in separate dosage unit form) and separately administered; in some embodiments, the limonoid compound (or a pharmaceutically acceptable derivative, ester, stereoisomer, salt or prodrug thereof) and the biguanide compound (or a pharmaceutically acceptable salt thereof) are administered simultaneously; in some embodiments, the limonoid compound (or a pharmaceutically acceptable derivative, ester, stereoisomer, salt or prodrug thereof) and the biguanide compound (or a pharmaceutically acceptable salt thereof) are administered one after another; in some embodiments, the limonoid compound (or a pharmaceutically acceptable derivative, ester, stereoisomer, salt or prodrug thereof) and the biguanide compound (or a pharmaceutically acceptable salt thereof) are administered one after another at a time interval of about 30 minutes, or about 1 hour, or about 2 hours, or about 4 hours, or about 8 hours, or about 12 hours. In some embodiments, as required, the combination product comprising the limonoid compound (or a pharmaceutically acceptable derivative, ester, stereoisomer, salt or prodrug thereof) and the biguanide compound (or a pharmaceutically acceptable salt thereof) according to the present invention that is in the form of pharmaceutical composition is administered for, including, but not limited to: 1, 2, 3, 4, 5 or 6 time(s) per day. In some embodiments, as required, the combination product comprising the limonoid compound (or a pharmaceutically acceptable derivative, ester, stereoisomer, salt or prodrug thereof) and the biguanide compound (or a pharmaceutically acceptable salt thereof) according to the present invention that is each in separate preparation form (preferably, each in separate dosage unit form) is administered for, including, but not limited to: 1, 2, 3, 4, 5 or 6 time(s) per day.

In a fourth aspect of the present invention, there is provided a method for preparing a combination product in the form of a pharmaceutical composition. In order to improve its operability as a drug or its absorbability when used in a living body, the limonoid compound or a pharmaceutically acceptable derivative, ester, stereoisomer, salt or prodrug thereof and the biguanide compound or a pharmaceutically acceptable salt thereof are preferably in combination with a pharmaceutical adjuvant such as a pharmaceutically acceptable carrier, excipient, diluent so as to form a preparation, thereby obtaining the form.

In a fifth aspect of the invention, there is provided a kit, the kit comprising the combination product described herein.

The term "pharmaceutically acceptable salt" as used throughout this description refers to a salt of a free acid or a free base, that is typically prepared by reacting the free base with a suitable organic or inorganic acid or by reacting the acid with a suitable organic or inorganic base. The term can be used for any compound, including 1,1-dimethyl biguanide and limonoid compounds (having the function of free acid or free base) and the like. Representative salts include: acetate, benzenesulfonate, benzoate, bicarbonate, bisulfate, hydrogen tartrate, borate, bromide, calcium edetate, camphorsulfonate, carbonate, chloride, clavulanate, citrate, dihydrochloride, edetate, ethanedisulfonate, estolate, esylate, fumarate, glucoheptonate, gluconate, glutamate, glycol lylarsanilate, hexylresorcinate, hydrabamine, hydrobromide, hydrochloride, hydroxynaphthoate, iodide, isethionate, lactate, lactobionate, laurate, malate, maleate, mandelate, methanesulfonate, methobromate (甲溴酸盐), methonitrate (甲硝酸盐) methosulfate, monopotassium maleate, mucate, naphthalenesulfonate, nitrate, N-methylglucosamine salt, oxalate, pamoate, palmitate, pantothenate, phosphate/bisphosphate, polygalacturonate, potassium salt, salicylate, sodium salt, stearate, subacetate, succinate, tannate, tartrate, teoclate, p-toluenesulfonate, triethiodide, trimethylamine salt, and valerate. When an acidic substituent is present, for example, —COOH, an ammonium salt, morpholine salt, sodium salt, potassium salt, barium salt, calcium salt, and the like can be formed for use in a dosage form. When a basic group is present (for example, in a limonoid compound or 1,1-dimethyl biguanide), such as an amino group or a basic heteroaryl group such as pyridyl, an acidic salt such as a hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, mesylate, ethanesulfonate, picrate, etc.

The source of the biguanide compound in the present invention may include, but is not limited to, metformin hydrochloride single tablet/capsule, metformin hydrochloride sustained-release tablet/capsule, metformin glibenclamide tablet/capsule, metformin hydrochloride enteric-coated tablet/capsule, metformin glipizide tablet/capsule, linagliptin metformin tablet/capsule, saxagliptin metformin sustained-release tablet/capsule, metformin gliclazide tablet/capsule, metformin pioglitazone tablet/capsule, sitagliptin metformin tablet/capsule, metformin vildagliptin tablet/capsule, repaglinide metformin tablet/capsule, metformin dapagliflozin tablet/capsule, metformin canagliflozin tablet/capsule, metformin empagliflozin tablet/capsule, metformin linagliptin tablet/capsule, metformin sitagliptin tablet/capsule, metformin alogliptin tablet/capsule, metformin pioglitazone tablet/capsule and the like.

SPECIFIC MODELS FOR CARRYING OUT THE INVENTION

The present invention is further described below through specific examples and comparative examples. However, it should be understood that these examples and comparative examples are only used for more detailed and specific explanation, and should not be understood as limiting the present invention in any form.

In the examples of the present invention, three diabetic mouse models and one obesity mouse model were used (the models were well known to those skilled in the art or were easily available according to conventional textbooks, technical manuals, and scientific literature in the art, including but not limited to the prior art documents exemplarily described in the examples) to simulate the pathological conditions of different stages of diabetes and the pathological conditions of obesity in humans. The limonoid compounds mentioned in the examples were present in the form of a monomer or an extract. The monomer was extracted or artificially synthesized, and its sources were commercially available, or they could be easily prepared and obtained by the prior art in the art.

EXAMPLE 1

Effects of a Limonoid Compound, Metformin or a Combination Thereof on Blood Glucose in a Mouse Pancreatic Islet β-Cell Injury Model In this example, a mouse pancreatic islet β-cell injury model was established by modeling ICR mice with streptozotocin (STZ) (referred to the prior art literature: Li Nan et al., Protective effect of pine pollen on kidney damage in diabetic nephropathy mice, Science and Technology Review, 2014, 32 (4/5): 95-99), and used to complete the evaluation of hypoglycemic effect in animals (this model could simulate pancreatic islet β-cell damage state of type I and type II diabetics). The limonoid compound was selected from the group consisting of limonin, isolimonic acid, limonin 17-β-D-glucopyranoside, and isolimonic acid 17-β-D-glucopyranoside, and a metformin single administration group, limonin single administration group, isolimonic acid single administration group, limonin 17-β-D-glucopyranoside singe administration group, isolimonic acid 17-β-D-glucopyranoside singe administration group, and combination thereof with metformin administration groups were set, respectively.

Conditions of experimental feeding: ICR mice (20±2 g), aged 6 weeks, purchased from Zhejiang Academy of Medical Sciences, and subjected to experimental feeding after 7 days of preliminary feeding. It should be noted that the conditions for raising the mice were as follows: the temperature was 23±1° C., the humidity was 55±10%, the lights were turned on between 7 am and 7 pm (the lights were turned off at other time), and the mice were allowed to access to water and feed freely. The experimental feed was mouse growth-stable feed (GB M2118), and the daily feeding and management of the animals were under the responsibility of the animal security department, which provided the animals with sufficient padding and fresh drinking water daily.

Experimental grouping: 15 male mice were randomly selected as the normal control group. After fasting for 12 hours, the remaining mice were intraperitoneally injected once with STZ at a dose of 150 mg/kg, and 72 hours later, the mice with blood glucose value of 15 to 25 mmol/L were undifferentiatedly grouped and used in the experiment, 15 animals in each group, and subjected to blood sampling and detection of indicators after two weeks of administration.

Gavage doses: the gavage dose was 0.02 g/kg per day for the limonin group, the gavage dose was 0.02 g/kg per day for the isolimonic acid group, the gavage dose was 0.02 g/kg per day for the limonin 17-β-D-glucopyranoside group, the gavage dose of metformin was 0.02 g/kg per day for the metformin group, limonin at a dose of 0.01 g/kg and metformin at a dose of 0.01 g/kg were simultaneously gavaged per day for the limonin/metformin combination group, isolimonic acid at a dose of 0.01 g/kg and metformin at a dose of 0.01 g/kg were simultaneously gavaged per day for the isolimonic acid/metformin combination group, limonin 17-β-D-glucopyranoside at a dose of 0.01 g/kg and metformin at a dose of 0.01 g/kg were simultaneously gavaged per day for the limonin 17-β-D-glucopyranoside/metformin combination group, isolimonic acid 17-β-D-glucopyranoside at a dose of 0.01 g/kg and metformin at a dose of 0.01 g/kg were simultaneously gavaged per day for the isolimonic acid 17-β-D-glucopyranoside/metformin combination group, the gavage volume was 10 mL/kg, and the normal group and the model group were administrated with 10 mL/kg of distilled water. Two weeks later, the blood glucose values were measured by tail trimming method (Johnson's blood glucose meter) 1 h after the last administration, and the average of each group was obtained. SPSS 16.0 software was used for statistical analysis. The data were expressed as mean and standard deviation. The data before and after were analyzed by t-test, and $P<0.05$ was considered statistically significant. The test results were shown in Table 1 below.

TABLE 1

Blood glucose values of STZ mice after two weeks of daily intragastric gavage.

| Group | Formulation and dose of administration | Blood glucose value (mmol/L) |
|---|---|---|
| Normal control group | None | 7.5 ± 0.61 |
| Model group | None | 29.5 ± 4.6 |
| Metformin group | Metformin 0.02 g/kg | 22.6 ± 3.9** |
| Limonin group | Limonin 0.02 g/kg | 19.5 ± 1.8** |
| Isolimonic acid group | Isolimonic acid 0.02 g/kg | 18.2 ± 3.1** |
| Limonin 17-β-D-glucopyranoside group | Limonin 17-β-D-glucopyranoside 0.02 g/kg | 18.9 ± 2.2** |
| Isolimonic acid 17-β-D-glucopyranoside group | Isolimonic acid 17-β-D-glucopyranoside 0.02 g/kg | 17.9 ± 2.8** |
| Limonin/metformin combination group | Limonin 0.01 g/kg + metformin 0.01 g/kg | 8.8 ± 3.1** |
| Isolimonic acid/metformin combination group | Isolimonic acid 0.01 g/kg + metformin 0.01 g/kg | 9.2 ± 3.3** |
| Limonin 17-β-D-glucopyranoside/metformin combination group | Limonin 17-β-D-glucopyranoside 0.01 g/kg + metformin 0.01 g/kg | 9.1 ± 3.6** |
| Isolimonic acid 17-β-D-glucopyranoside/metformin combination group | Isolimonic acid 17-β-D-glucopyranoside 0.01 g/kg + metformin 0.01 g/kg | 9.4 ± 2.3** |

Note
* After independent t-test, compared with the model group, the difference was extremely significant ($P < 0.05$)
**After independent t-test, compared with the model group, the difference was extremely significant ($P < 0.01$)

Discussion of Experimental Results

From the above results, it could be seen that, compared with the model group, either in single administration or in combination administration with metformin, limonin and its derivatives could significantly reduce the blood glucose values of the mice with STZ pancreatic islet cell injury. The administration of limonin and its derivatives in combination with metformin had significantly improved the effect as compared with their single administration, showing a synergistic effect. In addition, when limonin and its derivatives were administrated in combination with metformin, as compared with their single administration, the doses of both could be effectively reduced while comparable glucose-lowering effects could still be achieved, which improved the safety of therapeutic regimen and reduced side effects.

EXAMPLE 2

Effects of a Limonoid Compound, Metformin or a Combination Thereof on Blood Glucose and Leptin in a Mouse Model of Type II Diabetes In the present example, db/db mice (line name BKS.Cg-Dock7$^{m+/+}$ Lepr$^{db}$/Nju) were used to perform hypoglycemic efficacy evaluation test of animals (blood glucose level and leptin). The limonoid compound is selected from obacunone, isoobacunoic acid and obacunone 17-β-D-glucopynoside, and an obacunone single administration group, isoobacunoic acid single administration group, obacunone 17-β-D-glucopynoside single administered group, and combination thereof with metformin administration groups were set, respectively.

Conditions for experimental feeding: as type II diabetes model mice, 6-week-old SPF-grade db/db mice were purchased from the Nanjing Model Biology Institute, and subjected to experimental feeding after 7 days of preliminary feeding. It should be noted that the conditions for raising the mice were as follows: the temperature was 23±1° C., the humidity was 55±10%, the lights were turned on between 7 am and 7 pm (the lights were turned off at other time), and the mice were allowed to access to water and feed freely. The experimental feed was mouse growth-stable feed (GB M2118), and the daily feeding and management of the animals were under the responsibility of the animal security department, which provided the animals with sufficient padding and fresh drinking water daily.

Experimental grouping: male db/db mice (20±2 g) were selected, and 18 male mice in each group were tested. The experimental groups included the normal control group (db/m, n=18), the model group (db/db, n=18), the obacunone group (db/db, n=18), the isoobacunoic acid group (db/db, n=18), the obacunone 17-β-D-glucopynoside group (db/db, n=18), the metformin group (db/db, n=18), the obacunone/metformin combination group (db/db, n=18), the isoobacunoic acid/metformin combination group (db/db, n=18), the obacunone 17-β-D-glucopynoside/metformin combination group (db/db, n=18).

Gavage doses: obacunone at a dose of 0.04 g/kg was gavaged per day for the obacunone group, isoobacunoic acid at a dose of 0.04 g/kg was gavaged per day for the isoobacunoic acid group, obacunone 17-β-D-glucopynoside at a dose of 0.04 g/kg was gavaged per day for the obacunone 17-β-D-glucopynoside group, metformin at a dose of 0.04 g/kg was gavaged per day for the metformin group, obacunone at a dose of 0.02 g/kg and metformin at a dose of 0.02 g/kg were simultaneously gavaged per day for the obacunone/metformin combination group, isoobacunoic acid at a dose of 0.02 g/kg and metformin at a dose of 0.02 g/kg were simultaneously gavaged per day for the isoobacunoic acid/metformin combination group, obacunone 17-β-D-glucopynoside at a dose of 0.02 g/kg and metformin at a dose of 0.02 g/kg were simultaneously gavaged per day for the obacunone 17-β-D-glucopynoside/metformin combination group, the gavage volume was 10 mL/kg, and the normal group and the model group were administrated with 10 mL/kg of distilled water. Two weeks later, the blood glucose values were measured by tail trimming method (Johnson's blood glucose meter) 1 h after the last administration, and serum leptin levels were measured with blood collected from orbital cavity by enzyme-linked immunosorbent assay (Elisa), and the average of each group was obtained. SPSS 16.0 software was used for statistical analysis. The data were expressed as mean and standard deviation. The data before and after were analyzed by t-test, and $P<0.05$ was considered statistically significant. The test results were shown in Table 2 below.

TABLE 2

Blood glucose values and leptin of db/db mice after two weeks of daily gavage.

| Group | Formulation and dose of administration | Blood glucose value (mmol/L) | Leptin (pg/ml) |
|---|---|---|---|
| Normal control group | None | 6.0 ± 0.68 | 0.88 ± 0.18 |
| Model group | None | 23.9 ± 4.2 | 48.19 ± 8.12 |
| Obacunone group | Obacunone 0.04 g/kg | 12.71 ± 2.8** | 25.99 ± 3.92** |
| Isoobacunoic acid group | Isoobacunoic acid 0.04 g/kg | 14.66 ± 3.1** | 27.68 ± 3.25** |
| Obacunone 17-β-D-glucopynoside group | Obacunone 17-β-D-glucopynoside 0.04 g/kg | 13.67 ± 2.9** | 28.55 ± 4.00** |
| Metformin group | Metformin 0.04 g/kg | 15.5 ± 3.6** | 34.49 ± 3.38** |
| Obacunone/metformin combination group | Obacunone 0.02 g/kg + metformin 0.02 g/kg | 6.9 ± 2.2** | 18.42 ± 4.92** |
| Isoobacunoic acid/metformin combination group | Isoobacunoic acid 0.02 g/kg + metformin 0.02 g/kg | 7.5 ± 1.6** | 19.89 ± 3.67** |
| Obacunone 17-β-D-glucopynoside/metformin combination | Obacunone 17-β-D-glucopynoside 0.02 g/kg + metformin 0.02 g/kg | 7.3 ± 2.1** | 19.48 ± 3.71** |

Note
**after independent t-test, compared with the model group, the difference was extremely significant ($P < 0.01$)
* after independent t-test, compared with the model group, the difference was extremely significant ($P < 0.05$)

Discussion of Experimental Results

From the above results, it could be seen that, compared with the model group, either in single administration or in combination administration with metformin, obacunone and derivatives thereof could significantly reduce the blood glucose levels in the db/db diabetic mice. When obacunone and derivatives thereof were administrated in combination with metformin, significantly improved effect was observed relative to the single administration thereof, showing a synergistic effect. In addition, when obacunone and derivatives thereof were administrated in combination with metformin, as compared with their single administration, the doses of both could be effectively reduced while comparable glucose-lowering effects could still be achieved, which improved the safety of therapeutic regimen and reduced side effects.

Meanwhile, the limonoid compound represented by obacunone and its derivatives could significantly improve the sensitivity to leptin; and especially when administrated in combination with metformin, it could significantly improve the utilization efficiency of leptin in the body, improve the glucose metabolism of the body, and improve the functions relevant to the glucose metabolism in diabetes mice.

EXAMPLE 3

Effects of a Limonoid Compound, Metformin or a Combination Thereof on Blood Glucose in a Mouse Pancreatic Islet β-Cell Injury Model In this example, a mouse pancreatic islet β-cell injury model was established by modeling ICR mice with streptozotocin (STZ) (referred to the prior art literature: Li Nan et al., Protective effect of pine pollen on kidney damage in diabetic nephropathy mice, Science and Technology Review, 2014, 32 (4/5): 95-99), and used to complete the evaluation of hypoglycemic effect in animals (this model could simulate pancreatic islet β-cell damage state of type I and type II diabetics). The limonoid compound was selected from the group consisting of ichangin, ichangensin, and ichangin 17-β-D-glucopyranoside, and a metformin single administration group, ichangin single administration group, ichangensin single administration group, ichangin 17-β-D-glucopyranoside singe administration group, and combination thereof with metformin administration groups were set, respectively.

Conditions of experimental feeding: ICR mice (20±2 g), aged 6 weeks, purchased from Zhejiang Academy of Medical Sciences, and subjected to experimental feeding after 7 days of preliminary feeding. It should be noted that the conditions for raising the mice were as follows: the temperature was 23±1° C., the humidity was 55±10%, the lights were turned on between 7 am and 7 pm (the lights were turned off at other time), and the mice were allowed to access to water and feed freely. The experimental feed was mouse growth-stable feed (GB M2118), and the daily feeding and management of the animals were under the responsibility of the animal security department, which provided the animals with sufficient padding and fresh drinking water daily.

Experimental grouping: 15 male mice were randomly selected as the normal control group. After fasting for 12 hours, the remaining mice were intraperitoneally injected once with STZ at a dose of 150 mg/kg, and 72 hours later, the mice with blood glucose value of 15 to 25 mmol/L were undifferentiatedly grouped and used in the experiment, 15 animals in each group, and subjected to blood sampling and detection of indicators after two weeks of administration.

Gavage doses: the gavage dose was 0.1 g/kg per day for the ichangin group, the gavage dose was 0.1 g/kg per day for the ichangensin group, the gavage dose was 0.1 g/kg per day for the ichangin 17-β-D-glucopyranoside group, the gavage dose of metformin was 0.1 g/kg per day for the metformin group, ichangin at a dose of 0.05 g/kg and metformin at a dose of 0.05 g/kg were simultaneously gavaged per day for the ichangin/metformin combination group, ichangensin at a dose of 0.05 g/kg and metformin at a dose of 0.05 g/kg were simultaneously gavaged per day for the ichangensin/metformin combination group, ichangin 17-β-D-glucopyranoside at a dose of 0.05 g/kg and metformin at a dose of 0.05 g/kg were simultaneously gavaged per day for the ichangin 17-β-D-glucopyranoside/metformin combination group, the gavage volume was 10 mL/kg, and the normal group and the model group were administrated with 10 mL/kg of distilled water. Two weeks later, the blood glucose values were measured by tail trimming method (Johnson's blood glucose meter) 1 h after the last administration, and the average of each group was obtained. SPSS 16.0 software was used for statistical analysis. The data were expressed as mean and standard deviation. The data before and after were analyzed by t-test, and P<0.05 was considered statistically significant. The test results were shown in Table 3 below.

TABLE 3

Blood glucose values of STZ mice after two weeks of daily gavage.

| Group | Formulation and dose of administration | Blood glucose value (mmol/L) |
|---|---|---|
| Normal control group | None | 7.5 ± 0.61 |
| Model group | None | 29.5 ± 4.6 |
| Metformin group | Metformin 0.1 g/kg | 17.2 ± 3.9** |
| Ichangin group | Ichangin 0.1 g/kg | 14.8 ± 1.9** |
| Ichangensin group | Ichangensin 0.1 g/kg | 14.5 ± 3.5** |
| Ichangin 17-β-D-glucopyranoside group | Ichangin 17-β-D-glucopyranoside 0.1 g/kg | 14.9 ± 2.1** |
| Ichangin/metformin combination group | Ichangin 0.05 g/kg + metformin 0.05 g/kg | 7.7 ± 4.1** |
| Ichangensin/metformin combination group | Ichangensin 0.05 g/kg + metformin 0.05 g/kg | 7.6 ± 2.3** |
| Ichangin 17-β-D-glucopyranoside/metformin combination group | Ichangin 17-β-D-glucopyranoside 0.05 g/kg + metformin 0.05 g/kg | 8.0 ± 1.7** |

Note
**After independent t-test, compared with the model group, the difference was extremely significant (P < 0.01)
* After independent t-test, compared with the model group, the difference was extremely significant (P < 0.05)

Discussion of Experimental Results

From the above results, it could be seen that, compared with the model group, either in single administration or in combination administration with metformin, the three limonoid compounds all could significantly lower the blood glucose levels in the mice of the STZ pancreatic islet cell injury model. When they were administrated in combination with metformin, their effects were significantly increased as compared with their single administration, similar to the normal mice in blood glucose level, showing a synergistic effect. In addition, when the above three limonoid compounds were administration in combination with metformin, as compared with their single administration, the doses of both could be effectively reduced while comparable glucose-lowering effects could still be achieved, which improved the safety of therapeutic regimen and reduced side effects.

EXAMPLE 4

Effects of a Limonoid Compound, Metformin or a Combination Thereof on Blood Glucose and Insulin in a Mouse Model of Type II Diabetes In the present embodiment, the limonoid compound selected nomilin, deacetylnomilin, nomilin acid, deactylnomilin 17-β-D-glucopyranoside, and a nomilin single administration group, deacetylnomilin single administration group, nomilin acid single administered group, deactylnomilin 17-β-D-glucopyranoside single administration group, and combination thereof with metformin administration groups were set, respectively.

Conditions for experimental feeding: as type II diabetes model mice, 6-week-old SPF-grade db/db mice were purchased from the Nanjing Model Biology Institute, and subjected to experimental feeding after 7 days of preliminary feeding. It should be noted that the conditions for raising the mice were as follows: the temperature was 23±1° C., the humidity was 55±10%, the lights were turned on between 7 am and 7 pm (the lights were turned off at other time), and the mice were allowed to access to water and feed freely. The experimental feed was mouse growth-stable feed (GB M2118), and the daily feeding and management of the animals were under the responsibility of the animal security department, which provided the animals with sufficient padding and fresh drinking water daily.

Nomilin, deacetylnomilin, nomilin acid, deactylnomilin 17-β-D-glucopyranoside.

Experimental grouping: male db/db mice (20±2 g) were selected, 18 male mice in each group were tested, and drinking bottles were sterilized weekly. The experimental groups included the normal control group (db/m, n=18), the model group (db/db, n=18), the nomilin group (db/db, n=18), the deacetylnomilin group (db/db, n=18), the nomilin acid group (db/db, n=18), the deactylnomilin 17-β-D-glucopyranoside group (db/db, n=18), the metformin group (db/db, n=18), the nomilin/metformin combination group (db/db, n=18), the deacetylnomilin/metformin combination group (db/db, n=18), the nomilin acid/metformin combination group (db/db, n=18), the deactylnomilin 17-β-D-glucopyranoside/combination group (db/db, n=18).

Gavage doses: nomilin at a dose of 0.2 g/kg was gavaged per day for the nomilin group, deacetylnomilin at a dose of 0.2 g/kg was gavaged per day for the deacetylnomilin group, nomilin acid at a dose of 0.2 g/kg was gavaged per day for the nomilin acid group, deacetylnomilin 1743-D-glucopyranoside at a dose of 0.2 g/kg was gavaged per day for the deactylnomilin glucopyranoside group, metformin at a dose of 0.2 g/kg was gavaged per day for the metformin group, nomilin at a dose of 0.1 g/kg and metformin at a dose of 0.1 g/kg were simultaneously gavaged per day for the nomilin/metformin combination group, nomilin acid at a dose of 0.1 g/kg and metformin at a dose of 0.1 g/kg were simultaneously gavaged per day for the nomilin acid/metformin combination group, deacetylnomilin at a dose of 0.1 g/kg and metformin at a dose of 0.1 g/kg were simultaneously gavaged per day for the deacetylnomilin/metformin combination group, deactylnomilin 17-β-D-glucopyranoside at a dose of 0.1 g/kg and metformin at a dose of 0.1 g/kg were simultaneously gavaged per day for the deactylnomilin 17-β-D-glucopyranoside/metformin combination group, the gavage volume was 10 mL/kg, and the normal group and the model group were administrated with 10 mL/kg of distilled water. Two weeks later, the blood glucose values were measured by tail trimming method (Johnson's blood glucose meter) 1 h after the last administration, and serum insulin levels were measured with blood collected from orbital cavity by enzyme-linked immunosorbent assay (Elisa), and the average of each group was obtained. SPSS 16.0 software was used for statistical analysis. The data were expressed as mean and standard deviation. The data before and after were analyzed by t-test, and P<0.05 was considered statistically significant. The test results were shown in Table 4 below.

TABLE 4

Blood glucose values and insulin of db/db mice after two weeks of daily gavage.

| Group | Formulation and dose of administration | Blood glucose value (mmol/L) | Insulin (pg/ml) |
|---|---|---|---|
| Normal control group | None | 6.0 ± 0.68 | 1.05 ± 0.39 |
| Model group | None | 23.9 ± 4.2 | 10.56 ± 3.00 |
| Metformin group | Metformin 0.2 g/kg | 12.2 ± 3.6** | 8.19 ± 2.10** |
| Nomilin group | Nomilin acid 0.2 g/kg | 10.1 ± 2 2** | 8.82 ± 3.42** |
| Nomilin acid group | Nomilin acid 0.2 g/kg | 11.0 ± 4.1* | 8.08 ± 1 49** |
| deacetylnomilin group | deacetylnomilin 0.2 g/kg | 11.9 ± 2 9** | 8.59 ± 2.61** |
| deactylnomilin 17-β-D-glucopyranoside group | deactylnomilin 17-β-D-glucopyranoside 0.2 g/kg | 12.8 ± 5.5** | 8.40 ± 3.27** |
| Nomilin/metformin combination group | Nomilin 0.1 g/kg + metformin 0.1 g/kg | 6.2 ± 2.3** | 4.16 ± 3.33** |
| Nomilin acid/metformin combination group | Nomilin acid 0.1 g/kg + metformin 0.1 g/kg | 6.5 ± 3.5** | 5.49 ± 1.98** |
| deacetylnomilin/metformin combination group | deacetylnomilin 0.1 g/kg + metformin 0.1 g/kg | 6.6 ± 1.9** | 5.83 ± 3.90 |
| deactylnomilin 17-β-D-glucopyranoside/metformin combination group | deactylnomilin 17-β-D-glucopyranoside 0.1 g/kg + metformin 0.1 g/kg | 6.4 ± 1.2** | 5.17 ± 1.04** |

Note
**after independent t-test, compared with the model group, the difference was extremely significant ($P < 0.01$)
*after independent t-test, compared with the model group, the difference was extremely significant ($P < 0.05$)

Discussion of Experimental Results

From the above results, it could be seen that, compared with the model group, either in single administration or in combination administration with metformin, nomilin and derivatives thereof could significantly reduce the blood glucose levels in the db/db diabetic mice. When nomilin and derivatives thereof were administrated in combination with metformin, significantly improved effect was observed relative to the single administration thereof, showing a synergistic effect. In addition, when nomilin and derivatives thereof were administrated in combination with metformin, as compared with their single administration, the doses of both could be effectively reduced while comparable glucose-lowering effects could still be achieved, which improved the safety of therapeutic regimen and reduced side effects.

Meanwhile, the limonoid compound represented by nomilin and derivatives thereof could significantly improve the sensitivity to insulin; and especially when administrated in combination with metformin, it could significantly improve the utilization efficiency of insulin in the body, improve the glucose metabolism of the body, and improve the functions relevant to the glucose metabolism in diabetes mice.

EXAMPLE 5

Effects of a Limonoid Compound, Metformin or a Combination Thereof on Blood Glucose in a Mouse Model of Type II Diabetes with Pancreatic Islet Damage and Obesity In this example, a mouse model of type II diabetes with pancreatic islet damage and obesity was established by multiple modeling ICR mice with a small dose of streptozotocin (STZ), following with continuous high-fat diets (refer to the prior art literature: Zhang Jiyuan et al, Study on the effect of three plant extracts on improving glucose and lipid metabolism in type 2 diabetic mice, Food and Machinery, 2016, 32 (12): 142-147). The limonoid compound was selected from the group consisting of nomilin 17-β-D-glucopyranoside, deacetylnomilin 17-β-D-glucopyranoside, and nomilin acid 17-β-D-glucopyranoside, and a metformin single administration group, nomilin 17-β-D-glucopyranoside single administration group, deacetylnomilin single administration group, nomilinic acid 17-β-D-glucopyranoside single administration group, and combination thereof with metformin administration groups were set, respectively.

Conditions of experimental feeding: ICR mice (20±2 g), aged 6 weeks, purchased from Zhejiang Academy of Medical Sciences, and subjected to experimental feeding after 7 days of preliminary feeding. It should be noted that the conditions for raising the mice were as follows: the temperature was 23±1° C., the humidity was 55±10%, the lights were turned on between 7 am and 7 pm (the lights were turned off at other time), and the mice were allowed to access to water and feed freely. The experimental feed was mouse growth-stable feed (GB M2118), and the daily feeding and management of the animals were under the responsibility of the animal security department, which provided the animals with sufficient padding and fresh drinking water daily.

Experimental grouping: 15 male mice were randomly selected as the normal control group, and the remaining mice were subjected to a high-fat diet (high-fat diet formula: cholesterol 1%, egg yolk powder 10%, lard oil 10%, and basic feed 79%, for establishing an obesity mouse model) for consecutive 4 weeks and intraperitoneal injection of STZ at a dose of 35 mg/kg for three consecutive days. After one week, the mice were subject to 24 hours of fasting and water deprivation, their fasting blood glucose was measured, and the mice with a blood glucose level of 15 to 25 mmol/L were selected and undifferentiatedly grouped and used in the experiment, continuously subjected to the high-fat diet, 15 mice in each group, and subjected to blood sampling and detection of indicators after 3 weeks of administration.

Gavage doses: the gavage dose was 0.5 g/kg per day for the nomilin 17-β-D-glucopyranoside group, the gavage dose was 0.5 g/kg per day for the deacetylnomilin 17-β-D-glucopyranoside group, the gavage dose was 0.5 g/kg per day for the nomilinic acid 17-β-D-glucopyranoside group, metformin at a dose of 0.5 g/kg was gavaged per day for the metformin group, nomilin glucopyranoside at a dose of 0.25 g/kg and metformin at a dose of 0.25 g/kg were simultaneously gavaged per day for the nomilin 17-β-D-glucopyranoside/metformin combination group, deacetylnomilin 17-β-D-glucopyranoside at a dose of 0.25 g/kg and metformin at a dose of 0.25 g/kg were simultaneously gavaged per day for the deacetylnomilin glucopyranoside/metformin combination group, nomilinic acid 17-β-D-glucopyranoside at a dose of 0.25 g/kg and metformin at a dose of 0.25 g/kg were simultaneously gavaged per day for the nomilinic acid 17-β-D-glucopyranoside/metformin combination group, the gavage volume was 10 mL/kg, and the normal group and the model group were administered with 10 mL/kg of distilled water. Two weeks later, the blood glucose values were measured by tail trimming method (Johnson's blood glucose meter) 1 h after the last administration, and the average of each group was obtained. SPSS 16.0 software was used for statistical analysis. The data were expressed as mean and standard deviation. The data before and after were analyzed by t-test, and P<0.05 was considered statistically significant. The test results were shown in Table 5 below.

TABLE 5

Blood glucose values of STZ mice after three weeks of daily gavage.

| Group | Formulation and dose of administration | Blood glucose value (mmol/L) |
|---|---|---|
| Normal control group | None | 5.9 ± 0.54 |
| Model group | None | 29.6 ± 6.0 |
| Metformin group | Metformin 0.5 g/kg | 17.9 ± 3.6** |
| Nomilin 17-β-D-glucopyranoside group | Nomilin 17-β-D-glucopyranoside 0.5 g/kg | 12.8 ± 2.9** |
| Deacetylnomilin 17-β-D-glucopyranoside group | Deacetylnomilin 17-β-D-glucopyranoside 0.5 g/kg | 12.7 ± 2.5** |
| Nomilinic acid 17-β-D-glucopyranoside group | Nomilinic acid 17-β-D-glucopyranoside 0.5 g/kg | 13.5 ± 2.4** |
| Nomilin 17-β-D-glucopyranoside/metformin combination group | Nomilin 17-β-D-glucopyranoside 0.25 g/kg + metformin 0.25 g/kg | 5.8 ± 1.7** |
| Deacetylnomilin 17-β-D-glucopyranoside/metformin combination group | Deacetylnomilin 17-β-D-glucopyranoside 0.25 g/kg + metformin 0.25 g/kg | 6.3 ± 1.3** |
| Nomilinic acid 17-β-D-glucopyranoside/metformin combination group | Nomilinic acid 17-β-D-glucopyranoside 0.25 g/kg + metformin 0.25 g/kg | 6.0 ± 2.0** |

Note
**After independent t-test, compared with the model group, the difference was extremely significant (P < 0.01)
* After independent t-test, compared with the model group, the difference was extremely significant (P < 0.05)

Discussion of Experimental Results

From the above results, it could be seen that, compared with the model group, either in single administration or in combination administration with metformin, the three limonoid glycosides all could significantly lower the blood glucose levels in the mice of the STZ type II diabetes model. When they were administered in combination with metformin, their effects were significantly increased as compared with their single administration, similar to the normal mice in blood glucose level, showing a synergistic effect. In addition, when the above three limonoid glycosides were administration in combination with metformin, as compared with their single administration, the doses of both could be effectively reduced while comparable glucose-lowering effects could still be achieved, which improved the safety of therapeutic regimen and reduced side effects.

EXAMPLE 6

Effects of a Limonoid Compound, Metformin or a Combination Thereof on Body Weight, Triglycerides, and Total Cholesterol in an Obesity Mouse Model In this example, ICR mice were used to complete the experiment for evaluation of lipid lowering and weight loss in animals (body weight, serum cholesterol, and serum triglycerides).

In this example, the limonoid compound was nomilin, and a metformin single administration group, nomilin single administration group, and metformin/nomilin combination administration groups (dose A and B groups) were set, respectively.

Conditions of experimental feeding: ICR mice, purchased from the Animal Center of Zhejiang Academy of Medical Sciences, half male and half female, body weight (20±2 g), fed with basic feed provided by the Animal Center of Zhejiang Medical Academy. It should be noted that the conditions for raising the mice were as follows: the temperature was 23±1° C., the humidity was 55±10%, the lights were turned on between 7 am and 7 pm (the lights were turned off at other time), and the mice were allowed to access to water and feed freely. The daily feeding and management of the animals were under the responsibility of the animal security department, which provided the animals with sufficient padding and fresh drinking water daily.

The ICR mice were randomly divided into the normal group and the high-fat feed group, according to body weight. The normal group was fed with ordinary feed from the beginning to the end of the experiment. The rest of the animals were fed with a high-fat feed (high-fat diet formula: cholesterol 1%, egg yolk powder 10%, lard oil 10%, basic feed 79%, to establish a mouse model of obesity), body weight was measured after 3 weeks, in which the body weight of the animals in the high-fat feed group was higher than that in the normal control group, and t-test indicated that the data difference was significant and the modeling was successful (the data were not shown). The mice determined to have formed an obesity model were divided into a model control group (n=15), a nomilin control group (n=15), a metformin group (n=15), a of nomilin/metformin combination dose group A (n=15), and a nomiline/metformin combination dose group B (n=15).

Gavage dose: nomilin at a dose of 0.1 g/kg was gavaged per day for the nomilin group, metformin at a dose of 0.1 g/kg was gavaged per day for the metformin group, nomilin at a dose of 0.05 g/kg and metformin at a dose of 0.05 g/kg were simultaneously gavaged per day for the combination dose group A, nomilin at a dose of 0.1 g/kg and metformin at a dose of 0.1 g/kg were simultaneously gavaged per day for the combination dose group B, the gavage volume was 10 mL/kg, and the normal group and the model group were administered with 10 mL/kg of distilled water. Two weeks later, the mice were weighed, blood sampled from orbital cavity, measured to determine serum total cholesterol and triglyceride levels, and the average values of each group were obtained. SPSS 16.0 software was used for statistical analysis. The data were expressed as mean and standard deviation. The data before and after were analyzed by t-test, and P<0.05 was considered statistically significant. The test results were shown in Table 6 below.

TABLE 6

Weight gaining rate, serum triglycerides, and total cholesterol values of ICR mice after two weeks of daily gavage.

| Group | Formulation and dose of administration | Body weight gaining rate (%) | Triglycerides (mmol/L) | Total cholesterol (mmol/L) |
|---|---|---|---|---|
| Normal control group | None | 6.16 | 0.49 ± 0.19 | 1.67 ± 0.12 |
| Model group | None | 13.45 | 1.35 ± 0.17 | 3.49 ± 0.31 |
| Nomilin group | Nomilin 0.1 g/kg | 6.17 | 1.08 ± 0.33** | 3.09 ± 0.16* |
| Metformin group | Metformin 0.1 g/kg | 11.56 | 1.17 ± 0.30** | 3.35 ± 0.07 |
| Combination dose group A | Nomilin 0.05 g/kg + metformin 0.05 g/kg | 5.76 | 1.24 ± 0.28* | 3.15 ± 0.14* |
| Combination dose group B | Nomilin 0.1 g/kg + metformin 0.1 g/kg | 2.74 | 0.87 ± 0.46** | 2.60 ± 0.20** |

Note
**After independent t-test, compared with the model group, the difference was extremely significant ($P < 0.01$)
*After independent t-test, compared with the model group, the difference was extremely significant ($P < 0.05$)

Discussion of Experimental Results

From the above results, it could be seen that, compared with the model group, the weight gaining rate of the combination dose group A and the high-dose group B were much lower than that of the model group, and their effect was superior to that of the single administration group, and the dose group B had better effect, and the two drugs showed a synergistic effect; when maintaining essentially comparable indicators such as body weight gaining rate, total serum cholesterol, and serum triglycerides, the combination dose group A effectively reduced the dose of positive control metformin, thereby reducing the side effects and increasing the safety of therapeutic regimen. Therefore, the combination administration of limonoid compounds and biguanide compounds could effectively improve the effect of lipid lowering and weight loss.

EXAMPLE 7

Method for Preparing a Tablet Containing Combination Product of Nomilin and Metformin In this example, a method for preparing a tablet of a combination product (nomilin and metformin) of the present invention was exemplarily provided. A single tablet contained the following ingredients: 50 mg of nomilin, 400 mg of metformin hydrochloride, 20 mg of hydroxypropylmethylcellulose, 30 mg of sodium carboxymethylcellulose, and 20 mg of microcrystalline cellulose, 5.2 mg of magnesium stearate, 20.8 mg of Opadry, and there were a total of 1000 tablets.

The preparation method comprised the following steps:

a) dissolving 50 g of nomilin in 5 L of 50% ethanol;

b) passing the raw and auxiliary materials through 100 mesh sieves, leaving them on standby;

c) weighing 400 g of metformin hydrochloride, 20 g of hydroxypropylmethylcellulose, 30 g of sodium carboxymethylcellulose, and 20 g of microcrystalline cellulose, placing in a fluidized bed, and setting an inlet air volume of 500±50 m³/h, an inlet air temperature of 90±5° C., and a product temperature of 70±5° C., to perform hot melt granulation;

d) spraying a nomilin solution into the fluidized bed, setting an atomizing pressure of 1.0±0.2 bar, and a spraying speed of 30±10 Hz, to perform one-step granulation;

e) passing the resultant granules through a 1.0 mm round-hole screen to perform dry granulation;

f) adding 5.2 g of magnesium stearate and mixing for 5 min;

g) tabletting by using a 17×8.5 mm oval puncher at a pressure of 15 KN;

h) dissolving 20.8 g of Opadry 85F32004 in distilled water at a ratio of 1:4, setting parameters of a coating pan as: bed temperature of 40±2° C., air temperature of 48±2° C., atomizing pressure of 0.6 Mpa, pan speed of 7 rpm, spray volume of 120 g/min, to complete film coating.

What is claimed is:

1. A combination product, the combination product comprising a limonoid compound, or a pharmaceutically acceptable derivative or salt thereof, and a biguanide compound, or a pharmaceutically acceptable salt thereof, wherein the limonoid compound, or pharmaceutically acceptable derivative or salt thereof, is limonin, isolimonic acid, limonin 17-β-D-glucopyranoside, isolimonic acid 17-β-D-glucopyranoside, obacunone, obacunone 17-β-D-glucopynoside, ichangin, ichangensin, ichangin 17-β-D-glucopyranoside, nomilin, nomilin acid, deacetylnomilin, deacetylnomilin glucopyranoside, isoobacunoic acid, nomilin 17-β-D-glucopyranoside, or nomilinic acid 17-β-D-glucopyranoside, and the biguanide compound, or pharmaceutically acceptable salt thereof, is metformin or metformin hydrochloride.

2. The combination product according to claim 1, wherein the combination product is in the form of a pharmaceutical composition.

3. The combination product according to claim 1, wherein the limonoid compound, or a pharmaceutically acceptable derivative or salt thereof, and the biguanide compound, or a pharmaceutically acceptable salt thereof, are each in the form of a separate preparation.

4. The combination product according to claim 3, wherein the limonoid compound or a pharmaceutically acceptable derivative or salt thereof, and the biguanide compound, or a pharmaceutically acceptable salt thereof, are configured to be administered simultaneously or sequentially.

5. The combination product according to claim 1, wherein the biguanide compound, or a pharmaceutically acceptable salt thereof, is present in the combination product in an amount of 50 mg to 2000 mg.

6. The combination product according to claim 1, wherein the limonoid compound, or a pharmaceutically acceptable derivative or salt thereof, is present in the combination product in an amount of 50 mg to 2000 mg.

7. The combination product according to claim 1, wherein the combination product further comprises a pharmaceutically acceptable carrier, diluent, or excipient.

8. The combination product according to claim 7, wherein the combination product is in the form of a tablet, capsule, granule, syrup, powder, lozenge, sachet, cachet, elixir, suspension, emulsion, solution, syrup, aerosol, ointment, cream, or injection.

* * * * *

UNITED STATES PATENT AND TRADEMARK OFFICE
CERTIFICATE OF CORRECTION

| | |
|---|---|
| PATENT NO. | : 11,679,097 B2 |
| APPLICATION NO. | : 16/637018 |
| DATED | : June 20, 2023 |
| INVENTOR(S) | : Dong Li et al. |

It is certified that error appears in the above-identified patent and that said Letters Patent is hereby corrected as shown below:

In the Claims

At Column 20, Claim number 1, Lines 37 to 38:
"nomilin, nomilin acid, deacetylnomilin, deacetylnomilin glucopyranoside"

Should read:
-- nomilin, nomilin acid, deacetylnomilin, deacetylnomilin 17-β-D-glucopyranoside --

Signed and Sealed this
Twenty-ninth Day of August, 2023

Katherine Kelly Vidal
*Director of the United States Patent and Trademark Office*